US007700600B2

(12) United States Patent
Brown et al.

(10) Patent No.: US 7,700,600 B2
(45) Date of Patent: *Apr. 20, 2010

(54) METHODS FOR TREATING CARDIAC ARRHYTHMIA

(75) Inventors: Arthur M. Brown, Brecksville, OH (US); Naresh Chand, Gaithersburg, MD (US)

(73) Assignees: ChanTest, Inc., Cleveland, OH (US); United States of America, Washington, DC (US)

( * ) Notice: Subject to any disclaimer, the term of this patent is extended or adjusted under 35 U.S.C. 154(b) by 52 days.

This patent is subject to a terminal disclaimer.

(21) Appl. No.: 11/878,611

(22) Filed: Jul. 25, 2007

(65) Prior Publication Data
US 2008/0214554 A1 Sep. 4, 2008

Related U.S. Application Data

(63) Continuation of application No. 10/742,822, filed on Dec. 23, 2003, now abandoned, which is a continuation of application No. 10/079,485, filed on Feb. 22, 2002, now Pat. No. 6,743,797.

(51) Int. Cl.
*A61K 31/496* (2006.01)
(52) U.S. Cl. .................................................. 514/255.04
(58) Field of Classification Search ............. 514/255.04
See application file for complete search history.

(56) References Cited

U.S. PATENT DOCUMENTS

| 4,202,896 | A | 5/1980 | Gootjes |
| 4,476,129 | A | 10/1984 | Gootjes et al. |
| 4,874,765 | A | 10/1989 | Lapis et al. |
| 6,187,802 | B1 | 2/2001 | Cheetham et al. |
| 6,743,797 | B2 | 6/2004 | Brown et al. |
| 7,034,008 | B2 | 4/2006 | Donahue et al. |

FOREIGN PATENT DOCUMENTS

| EP | 0 243 903 | 11/1987 |
| WO | WO 91/01732 | 2/1991 |

OTHER PUBLICATIONS

Http:en/wikipedia.org/wiki/Cardia_arrhythmia (2008).*
Lewis et al., Journal of Medicinal Chemistry, vol. 42, No. 24, pp. 5029-5042 (1999).*
Miller, "Cocaine", American Family Physician, vol. 39, No. 2, pp. 115-120 (Feb. 1989).*
"RF Catheter Ablation: An Innovative Treatment for Atrial Fibrillation", Hakan Oral, medical News Today, 2004.
"Better, Faster Arrhythmia Treatment", The George Washington University Hospital's Health News, www/gwhospital.com, 2001.
"Advances in the Treatment of Atrial Tachyarrhythmias", Israel et al., abstract, www.blackwellpublishing.com, 2006.
Heikkila et al., European Journal of Pharmacology, 1984, 103(3-4), 241-8.
"Controlling Potassium Channel Activites: Interplay between the membrane and intracellular factors", Yi et al., PNAS, vol. 98, No. 20, pp. 11016-11023, 2001.
"Dopamine Stimulation of Cardiac .beta.-adrenoceptors : the involvement of sympathetic amine transporters and the effect of SKF38393", British Journal of Pharmacology, 1997, 122/8, 1669-1678.
"Effects of cocaine and GBR 12909 on cardiac functioning in rhesus monkeys", Society for Neuroscience, abstracts, 1998, vol. 24, No. 1-2, pp. 2170.
Balser, J. R. et al., "Suppression of time-dependent outward current in guinea pig ventricular myocytes: Actions of quinidine and amiodarone", Circ. Res. 69:519-529 (1991).
Funck-Bretano, C. "Rate dependence of class III actions in the heart", Fundam. Clin. Pharmacol. 7:51-59 (1993).
Curran, M.E. et al., "A molecular basis for cardiac arrhythmia: HERG mutations cause long QT syndrome", Cell 80: 795-803 (1995).
Dutta, A.K. et al., "Positional Importance of the Nitrogen Atom in Novel Piperidine Analogs of GBR 12909: Affinity and Selectivity for the Dopamine Transporter", Med. Chem. Res. 3:209-222 (1993).
Hondeghem, L. M., "Development of Class III Antiarrhythmic Agents", J. Cardiovasc. Pharmacol. (20) (Suppl. 2):S17-S22 (1992).
Hondeghem, L.M. et al., "Class III antiarrhythmic agents have a lot of potential but a long way to go: Reduced effectiveness and dangers of reverse use dependence", Circulation, 81:686-690 (1990).
Jurkiewicz, N.K. et al., "Rate-dependent prolongation of cardiac action potentials by a methanesulfonanilide class III anti-arrhythmic agent: Specific block of rapidly activating delayed rectifier K+ current by dofetilide", Circ .Res. 72:75-83 (1993).
Lewis, D.B. et al., "Oxygenated analogues of 1-(2-(diphenylmethoxy) ethyl)- and 1-(2-(bis(4-fluorophenyl) methoxy)ethyl)-4-(3-phenylpropyl) piperazines (GBR 12935 and GBR 12909) as Potential Extended-Action Cocaine-Abuse Therapeutic Agents", J. Med. Chem. 42:5029-5042 (1999).
Nademanee, K., "The Aminodarone Odyssey", J. Am. Coll. Cardiol. 20:1063-1065 (1992).
Roden, D. M. et al., "Current Status of Class III Antiarrhythmic Drug Therapy", Am. J. Cardiol, 72:44B-49B (1993).
Sadanaga, T. et al., "Clinical evaluation of the use-dependent QRS prolongation and the reverse use-dependent QT prolongation of class I and class III anti-arrhythmic agents and their value in predicting efficacy", Am. Heart J. 126:114-121 (1993).
Sanguinetti, M.C. et al., "Two components of cardiac delayed rectifier K+ current. Differential sensitivity to block by Class III anti-arrythmic agents", J. Gen. Physiol. 96:195-215 (1990).
Singh B. N., et al., "The effect of amiodarone, a new anti-anginal drug, on cardiac muscle", Br. J. Pharmacol 39:657-667 (1970).

(Continued)

Primary Examiner—Kevin Weddington
(74) Attorney, Agent, or Firm—Duane Morris LLP

(57) ABSTRACT

Disclosed are methods of preventing or treating cardiac arrhythmia comprising administering to a mammal in need thereof, such as a human, an effective amount of vanoxerine (GBR 12909) or a pharmaceutically acceptable salt, derivative or metabolite thereof.

5 Claims, No Drawings

OTHER PUBLICATIONS

Singh B. N., et al., "A third class of anti-arrhythmic action effects on atrial and ventricular intracellular potentials, and other pharmacological actions on cardiac muscle, of MJ 1999 and AH 3747", Br. J. Pharmacol 39:675-687 (1970).

Williams, E.M.V. et al., "Classification of antiarrhythmic drugs", Symposium on Cardiac Arrhythmias, (Sandoe E. et al., (Editors)) Chapter 20, pp. 449-472 (1981).

Maginn et al., "Protective Effects of Vanoxeamine (GBR 12909) Against Ischemia-Induced Hyperactivity and Neurodegeneration in the Gerbil Model of Cerebral Ischemia,", abstract, Pharmacology, Biochemistry and Behavior, 1997, 56(4), pp. 727-735.

Nielsen-Kidsk et al., "Myocardial Accumulation Kinetics and Pharmacodynamics in the Isolated Rabit Heart of a New Inhibitor of Dopamine Reuptake, GBR 12909," abstract, Pharmacology & Toxicology (Oxford, United Kingdom), 1990, 66(3), pp. 197-202.

Ficker et al., "The Binding Site for Channel Blockers that Rescue Misprocessed Human Long QT Syndrome Type 2 Ether-A-Gogo-Related Gene (HERG) Mutations," abstract, Journal of Biological Chemistry, 2002, 277(7), pp. 4989-4998.

Thomas et al., "High-Affinity Blockade of Human Ether-A-Go-Related Gene Human Cardiac Potassium Channels by the Novel Antiarrhythmic Drug BRL-32872," abstract, Journal of Pharmacology and Experimental Therapeutics, 2001, 297(2), pp. 753-761.

* cited by examiner

METHODS FOR TREATING CARDIAC ARRHYTHMIA

This is a continuation of U.S. patent application Ser. No. 10/742,822 filed Dec. 23, 2003 now abandoned, which is a continuation of U.S. patent application Ser. No. 10/079,485 filed on Feb. 22, 2002 now U.S. Pat. No. 6,743,797.

BACKGROUND OF THE INVENTION

1. Field of the Invention

The present invention relates to methods of preventing or treating cardiac arrhythmia comprising administering to a mammal in need thereof an effective amount of vanoxerine (GBR 12909) or a pharmaceutical acceptable salt, derivative or metabolite thereof.

2. Background of the Related Art

Atrial flutter and/or atrial fibrillation (AF) are the most commonly sustained cardiac arrhythmias in clinical practice, and are likely to increase in prevalence with the aging of the population. Currently, AF affects more than 1 million Americans annually, represents over 5% of all admissions for cardiovascular diseases and causes more than 80,000 strokes each year in the United States. While AF is rarely a lethal arrhythmia, it is responsible for substantial morbidity and can lead to complications such as the development of congestive heart failure or thromboembolism. Currently available Class I and Class III anti-arrhythmic drugs reduce the rate of recurrence of AF, but are of limited use because of a variety of potentially adverse effects, including ventricular proarrhythmia. Because current therapy is inadequate and fraught with side effects, there is a clear need to develop new therapeutic approaches.

Ventricular fibrillation (VF) is the most common cause associated with acute myocardial infarction, ischemic coronary artery disease and congestive heart failure. AS with AF, current therapy is inadequate and there is a need to develop new therapeutic approaches.

Although various anti-arrhythmic agents are now available on the market, those having both satisfactory efficacy and a high margin of safety have not been obtained. For example, anti-arrhythmic agents of Class I, according to the classification scheme of Vaughan-Williams ("Classification of antiarrhythmic drugs", Cardiac Arrhythmias, edited by: E. Sandoe, E. Flensted-Jensen, K. Olesen; Sweden, Astra, Sodertalje, pp 449-472 (1981)), which cause a selective inhibition of the maximum velocity of the upstroke of the action potential ($V_{max}$) are inadequate for preventing ventricular fibrillation because they shorten the wave length of the cardiac action potential, thereby favoring re-entry. In addition, they have problems regarding safety, i.e. they cause a depression of myocardial contractility and have a tendency to induce arrhythmias due to an inhibition of impulse conduction. The CAST (coronary artery suppression trial) study was terminated while in progress because the Class I antagonists had a higher mortality than placebo controls. β-adrenergenic receptor blockers and calcium channel ($I_{Ca}$) antagonists, which belong to Class II and Class IV, respectively, have a defect in that their effects are either limited to a certain type of arrhythmia or are contraindicated because of their cardiac depressant properties in certain patients with cardiovascular disease. Their safety, however, is higher than that of the anti-arrhythmic agents of Class I.

Anti-arrhythmic agents of Class III are drugs that cause a selective prolongation of the action potential duration (APD) without a significant depression of the maximum upstroke velocity ($V_{max}$). They therefore lengthen the save length of the cardiac action potential increasing refractories, thereby antagonizing re-entry. Available drugs in this class are limited in number. Examples such as sotalol and amiodarone have been shown to possess interesting Class III properties (Singh B. N., Vaughan Williams E. M., "A third class of anti-arrhythmic action: effects on atrial and ventricular intracellular potentials and other pharmacological actions on cardiac muscle of MJ 1999 and AH 3747", Br. J. Pharmacol 39:675-689 (1970), and Singh B. N., Vaughan Williams E. M., "The effect of amiodarone, a new anti-anginal drug, on cardiac muscle", Br. J. Pharmacol 39:657-667 (1970)), but these are not selective Class III agents.

Sotalol also possesses Class I (β-adrenergic blocking) effects which may cause cardiac depression and is contraindicated in certain susceptible patients.

Amiodarone also is not a selective Class III antiarrhythmic agent because it possesses multiple electrophysiological actions and is severely limited by side effects. (Nademanee, K., "The Amiodarone Odyssey", J. Am. Coll. Cardiol. 20:1063-1065 (1992)) Drugs of this class are expected to be effective in preventing ventricular fibrillation. Selective Class III agents, by definition, are not considered to cause myocardial depression or an induction of arrhythmias due to inhibition of conduction of the action potential as seen with Class I antiarrhythmic agents.

Class III agents increase myocardial refractoriness via a prolongation of cardiac action potential duration (APD). Theoretically, prolongation of the cardiac action potential can be achieved by enhancing inward currents (i.e. Na+ or Ca²+ currents; hereinafter $I_{Na}$ and $I_{Ca}$, respectively) or by reducing outward repolarizing potassium K+ currents. The delayed rectifier ($I_K$) K+ current is the main outward current involved in the overall repolarization process during the action potential plateau, whereas the transient outward ($I_{to}$) and inward rectifier ($I_{KI}$) K+ currents are responsible for the rapid initial and terminal phases of repolarization, respectively. Cellular electrophysiologic studies have demonstrated that $I_K$ consists of two pharmacologically and kinetically distinct K+ current subtypes, $I_{Kr}$ (rapidly activating and deactivating and $I_{Ks}$ (slowly activating and deactivating). (Sanguinetti and Jurkiewicz, "Two components of cardiac delayed rectifier K+ current. Differential sensitivity to block by Class III anti-arrhythmic agents", J Gen. Physiol 96:195-215 (1990)). $I_{Kr}$ is also the product of the human ether-a-go-go gene (hERG). Expression of hERG cDNA in cell lines leads to production of the hERG current which is almost identical to $I_{Kr}$ (Curran et al., "A molecular basis for cardiac arrhythmia: hERG mutations cause long QT syndrome," Cell 80(5):795-803 (1995)).

Class III anti-arrhythmic agents currently in development, including d-sotalol, dofetilide (UK-68,798), almokalant (H234/09), E-4031 and methanesulfonamide-N-[1'-6-cyano-1,2,3,4-tetrahydro-2-naphthalenyl)-3,4-dihydro-4-hydroxyspiro[2H-1-benzopyran-2,4'-piperidin]-6-yl], (+)-, monochloride (MK-499) predominantly, if not exclusively, block $I_{Kr}$. Although, amiodarone is a blocker of $I_{Ks}$ (Balser J. R. Bennett, P. B., Hondeghem, L. M. and Roden, D. M. "Suppression of time-dependent outward current in guinea pig ventricular myocytes: Actions of quinidine and amiodarone", *Circ. Res.* 69:519-529 (1991)), it also blocks $I_{Na}$ and $I_{Ca}$, effects thyroid function, is as a nonspecific adrenergic blocker, acts as an inhibitor of the enzyme phospholipase, and causes pulmonary fibrosis (Nademanee, K "The Amiodarone Odessey". *J. Am. Coll. Cardiol.* 20:1063-1065 (1992)).

Reentrant excitation (reentry) has been shown to be a prominent mechanism underlying supraventricular arrhythmias in man. Reentrant excitation requires a critical balance between slow conduction velocity and sufficiently brief refractory periods to allow for the initiation and maintenance of multiple reentry circuits to coexist simultaneously and sustain AF. Increasing myocardial refractoriness by prolonging APD, prevents and/or terminates reentrant arrhythmias. Most selective, class III antiarrhythmic agents currently in development, such as d-sotalol and dofetilide predominantly, if not exclusively, block $I_{Kr}$, the rapidly activating component of $I_K$ found both in atrium and ventricle in man.

Since these $I_{Kr}$ blockers increase APD and refractoriness both in atria and ventricle without affecting conduction per se, theoretically they represent potential useful agents for the treatment of arrhythmias-like AF and VF. These agents have a liability in that they have an enhanced risk of proarrhythmia at slow heart rates. For example, torsade de pointes, a specific type of polymorphic ventricular tachycardia which is commonly associated with excessive prolongation of the electrocardigraphic QT interval, hence termed "acquired long QT syndrome", has been observed when these compounds are utilized (Roden, D. M. "Current Status of Class III Antiarrhythmic Drug Therapy", *Am J. Cardiol,* 72:44B-49B (1993)). The exaggerated effect at slow heart rates has been termed "reverse frequency-dependence" and is in contrast to frequency-independent or frequency-dependent actions. (Hondeghem, L. M., "Development of Class III Antiarrhythmic Agents", *J. Cardiovasc. Cariol.* 20 (Suppl. 2):S17-S22). The pro-arrhythmic tendency led to suspension of the SWORD trial when d-sotalol had a higher mortality than placebo controls.

The slowly activating component of the delayed rectifier ($I_{Ks}$) potentially overcomes some of the limitations of $I_{Kr}$ blockers associated with ventricular arrhythmias. Because of its slow activation kinetics, however, the role of $I_{Ks}$ in atrial repolarization may be limited due to the relatively short APD of the atrium Consequently, although $I_{Ks}$ blockers may provide distinct advantage in the case of ventricular arrhythmias, their ability to affect supra-ventricular tachyarrhythmias (SVT) is considered to be minimal.

Another major defect or limitation of most currently available Class III anti-arrhythmic agents is that their effect increases or becomes more manifest at or during bradycardia or slow heart rates, and this contributes to their potential for proarrhythmia. On the other hand, during tachycardia or the conditions for which these agents or drugs are intended and most needed, they lose most of their effect. This loss or diminishment of effect at fast heart rates has been termed "reverse use-dependence" (Hondeghem and Snyders, "Class III antiarrhythmic agents have a lot of potential but a long way to go: Reduced effectiveness and dangers of reverse use dependence", *Circulation* 81:686-690 (1990); Sadanaga et al., "Clinical evaluation of the use-dependent QRS prolongation and the reverse use-dependent QT prolongation of class III anti-arrhythmic agents and their value in predicting efficiency" *Amer. Heart Journal* 126:114-121 (1993)), or "reverse rate-dependence" (Bretano, "Rate dependence of class III actions in the heart", *Fundam. Clin. Pharmacol.* 7:51-59 (1993); Jurkiewicz and Sanguinetti, "Rate-dependent prolongation of cardiac action potentials by a methanesulfonanilide class III anti-arrhythmic agent: Specific block of rapidly activating delayed rectifier K+ current by dofetilide", *Circ. Res.* 72:75-83 (1993)). Thus, an agent that has a use-dependent or rate-dependent profile, opposite that possessed by most current class III anti-arrhythmic agents, should provide not only improved safety but also enhanced efficacy.

In view of the problems associated with current class III anti-arrhythmic agents, there remains a need for an effective treatment of cardiac arrhythmias in mammals. The above references are incorporated by reference herein where appropriate for appropriate teachings of additional or alternative details, features and/or technical background.

SUMMARY OF THE INVENTION

Accordingly, it is an object of the present invention to provide methods of preventing or treating cardiac arrhythmia in a mammal. Other objects, features and advantages of the present invention will be set forth in the detailed description of preferred embodiments that follows, and in part will be apparent from the description or may be learned by practice of the invention. These objects and advantages of the invention will be realized and attained by the compositions and methods particularly pointed out in the written description and claims hereof.

In accordance with these and other objects, a first embodiment of the present invention is directed to a method for preventing cardiac arrhythmia comprising administering to a mammal in need thereof an effective amount of vanoxerine (GBR 12909), or a pharmaceutically acceptable salt, derivative or metabolite thereof.

A second embodiment of the present invention is directed to a method for treating cardiac arrhythmia comprising administering to a mammal in need thereof an effective amount of vanoxerine, or a pharmaceutically acceptable salt, derivative or metabolite thereof.

A third embodiment of the present invention is directed to a method for modulating the activity of at least one ion channel of a mammalian cell comprising contacting a mammalian cell with an effective amount of vanoxerine, or a pharmaceutically acceptable salt, derivative or metabolite thereof.

A fourth embodiment of the present invention is directed to a pharmaceutical composition for the prevention of cardiac arrhythmia in a mammal, such as a human, comprising an effective amount of vanoxerine, or a pharmaceutically acceptable salt, derivative or metabolite thereof, and a pharmaceutically acceptable carrier.

A fifth embodiment of the present invention is directed to a pharmaceutical composition for the treatment of cardiac arrhythmia in a mammal, such as a human, comprising an effective amount of vanoxerine, or a pharmaceutically acceptable salt, derivative or metabolite thereof, and a pharmaceutically acceptable carrier.

A sixth embodiment of the present invention is directed to a method of screening for compounds that bind to $I_{Kr}$ or hERG comprising: (i) contacting a mammalian cell that stably expresses $I_{Kr}$ or hERG with labeled vanoxerine, or a pharmaceutically acceptable salt, derivative or metabolite thereof, to form a labeled binding pair, (ii) contacting the labeled binding pair with a compound of interest; and (iii) determining whether the compound of interest displaces the labeled vanoxerine, or the pharmaceutically acceptable salt, derivative or metabolite thereof.

DETAILED DESCRIPTION OF PREFERRED EMBODIMENTS

As used herein, the singular forms "a," "an," and "the" include the plural reference unless the context clearly dictates otherwise.

Among the preferred embodiments of the present invention are methods of preventing or treating cardiac arrhythmia. Each of these methods comprises the step of administering to a mammal in need thereof, such as a human in need thereof, an effective amount of vanoxerine, or a pharmaceutically acceptable salt, derivative or metabolite thereof. The preferred embodiments of the present invention also include compositions for preventing or treating cardiac arrhythmia in a mammal, such as a human, comprising vanoxerine, or a pharmaceutically acceptable salt, derivative or metabolite thereof, and a pharmaceutically acceptable carrier.

Vanoxerine (also known as GBR-12909) is a compound having the following structural formula:

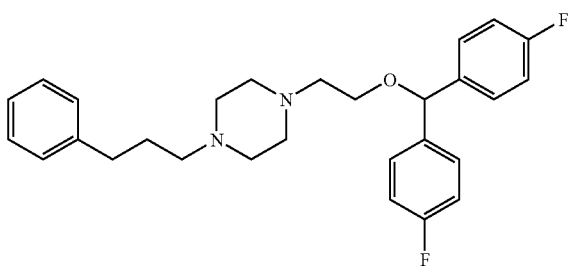

Vanoxerine, its manufacture and/or certain pharmaceutical uses thereof are described in U.S. Pat. Nos. 4,202,896, 4,476,129 and 4,874,765, as well as European Patent EP 243,903 and PCT International Application WO 91/01732, each of which is incorporated herein by reference.

In the past, vanoxerine has been used for treating cocaine addiction, acute effects of cocaine, and cocaine cravings in mammals, as well as dopamine agonists for the treatment of Parkinsonism, acromegaly, hyperprolactinemia and diseases arising from a hypofunction of the dopaminergic system. (See U.S. Pat. No. 4,202,896 and WO 91/01732.) While vanoxerine has been found useful in the treatment of diseases arising from a decrease in the dopamine level, i.e. from the hypofunction of the dopaminergic system, and is known to be a high affinity blocker of dopamine reuptake, vanoxerine has not been used in other types of therapies.

Pharmaceutically acceptable salts of vanoxerine may also be employed in the methods of the present invention. The pharmaceutically acceptable salts of vanoxerine which may be used in the inventive methods include, but are not limited to, salts of vanoxerine formed from non-toxic inorganic or organic acids. For example, pharmaceutically acceptable salts include, but are not limited to, the following: salts derived from inorganic acids, such as hydrochloric, hydrobromic, sulfuric, sulfamic, phosphoric, nitric and the like; salts derived from organic acids, such as acetic, propionic, succinic, glycolic, stearic, lactic, malic, tartaric, citric, ascorbic, pamoic, maleic, hydroxymaleic, phenylacetic, benzoic, salicylic, sulfanilic, 2-acetoxy-benzoic, fumaric, toluenesulfonic, methanesulfonic, ethane disulfonic, oxalic, isethionic, trifluoroacetic and the like; and salts derived from ammo acids, such as glutamic acid or aspartic acid. See U.S. Pat. No. 6,187,802 and WO 91/01732.

The pharmaceutically acceptable salts of vanoxerine useful in the methods of the present invention can be synthesized from vanoxerine by conventional chemical methods. Generally, the salts are prepared either by ion exchange chromatography or by reacting the free base with stoichiometric amounts or with an excess of the desired salt-forming inorganic or organic acid in a suitable solvent or various combinations of solvents.

Pharmaceutically acceptable metabolites of vanoxerine may be employed in the methods of the present invention, provided that they elicit the necessary pharmacological response(s) when administered to a mammal, such as a human, and are otherwise appropriate for use in the invention methods, e.g., exhibit an acceptable toxicology profile, are relatively stable under the conditions of use, etc. Illustrative examples of suitable metabolite which may be employed in the inventive methods include, but are not limited to, the following: 1-[2-(diphenylmethoxy)ethyl]-4-(3-phenylpropyl)piperazine (which is also known as GBR 12935 and is the principal metabolite of vanoxerine in humans) and pharmaceutically acceptable salts, analogs and derivatives thereof.

Pharmaceutically acceptable derivatives of vanoxerine may also be employed in the methods of the present invention, provided that they elicit the necessary pharmacological responses when administered to a mammal, such as a human, and are otherwise appropriate for use in the invention methods, e.g., exhibit an acceptable toxicology profile, are relatively stable under the conditions of use, etc. Illustrative examples of suitable derivatives which may be employed in the inventive methods include, but are not limited to, the following: GBR 13069 and GBR 12783, which are structurally similar to vanoxerine and GBR 12935, respectively, except that the 3-phenylpropyl moiety has been replaced by a 3-phenylpropen-2-yl moiety.

Other suitable derivatives include phenolic derivatives of vanoxerine, i.e. derivatives of vanoxerine in which the unsubstituted phenyl group of vanoxerine is substituted by one or more hydroxy groups, as well as the methoxy congeners thereof. (See Rice et al., "Oxygenated analogues of 1-(2-(diphenylmethoxy)ethyl)- and 1-(2-(bis(4-fluorophenyl)methoxy)ethyl)-4-(3-phenylpropyl) piperazines (GBR 12935 and GBR 12909) as Potential Extended-Action Cocaine-Abuse Therapeutic Agents," *J. Med. Chem.* 42(23): 5029-5042 (2001); and Dutta et al., "Positional Importance of the Nitrogen Atom in Novel Piperidine Analogs of GBR 12909: Affinity and Selectivity for the Dopamine Transporter," *Med. Chem. Res.* 3(4):209-222 (1993), both of which are incorporated by reference.)

Additional examples of suitable derivatives which may be employed in the methods of the present invention include 4-[2-bis(halophenyl)methoxy]-ethyl]-α-(substituted phenyl)-1-piperazine alkanol derivatives of the general formula:

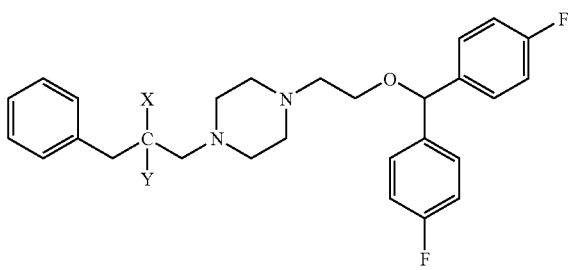

where X represents a hydroxy, $C_{1-4}$ alkoxy, phenylcarbamoyloxy or $C_{1-4}$ alkylcarbamoyloxy group, and Y represents a hydrogen atom or a $C_{1-3}$ alkyl group, or X and Y together with the carbon atom to which they are linked represent a carbonyl group. See U.S. Pat. No. 4,476,129.

When employed in the present methods, vanoxerine, or a pharmaceutically acceptable salt, derivative or metabolite thereof, may be administered by any technique capable of introducing a pharmaceutically active agent to the desired site of action, including, but not limited to, buccal, sublingual, nasal, oral, topical, rectal and parenteral administration. Delivery of the compound may also be through the use of controlled release formulations in subcutaneous implants or transdermal patches.

For oral administration, a suitable composition containing vanoxerine, or a pharmaceutically acceptable salt, derivative or metabolite thereof, may be prepared in the form of tablets, dragees, capsules, syrups and aqueous or oil suspensions. The inert ingredients used in the preparation of these compositions are known in the art. For example, tablets may be prepared by mixing the active compound with an inert diluent, such as lactose or calcium phosphate, in the presence of a disintegrating agent, such as potato starch or microcrystalline cellulose, and a lubricating agent, such as magnesium stearate or talc, and then tableting the mixture by known methods.

Tablets may also be formulated in a manner known in the art so as to give a sustained release of vanoxerine, or a pharmaceutically acceptable salt, derivative or metabolite thereof. Such tablets may, if desired, be provided with enteric coatings by known method, for example by the use of cellulose acetate phthalate. Suitable binding or granulating agents are e.g. gelatine, sodium carboxymethylcellulose, methylcellulose, polyvinylpyrrolidone or starch gum. Talc, colloidal silicic acid, stearin as well as calcium and magnesium stearate or the like can be used as anti-adhesive and gliding agents.

Tablets may also be prepared by wet granulation and subsequent compression. A mixture containing the vanoxerine, or a pharmaceutically acceptable salt, derivative or metabolite thereof, and at least one diluent, and optionally a part of the disintegrating agent, is granulated together with an aqueous, ethanolic or aqueous-ethanolic solution of the binding agents in an appropriate equipment, then the granulate is dried. Thereafter, other preservative, surface acting, dispersing, disintegrating, gliding and anti-adhesive additives can be mixed to the dried granulate and the mixture can be compressed to tablets or capsules.

The tablets may also be prepared by the direct compression of the mixture containing the active ingredient together with the needed additives. If desired, the tablets may be transformed to dragees by using protective, flavoring and dyeing agents such as sugar, cellulose derivatives (methyl- or ethylcellulose or sodium carboxymethylcellulose), polyvinlpyrrolidone, calcium phosphate, calcium carbonate, food dyes, aromatizing agents, iron oxide pigments and the like which are commonly used in the pharmaceutical industry.

For the preparation of capsules or caplets, a mixture of vanoxerine, or a pharmaceutically acceptable salt, derivative or metabolite thereof, and the desired additives may be filled into a capsule, such as a hard or soft gelatin capsule. The contents of a capsule and/or caplet may also be formulated using known methods to give sustained release of the active compound.

Liquid oral dosage forms of vanoxerine, or a pharmaceutically acceptable salt, derivative or metabolite thereof, may be an elixir, suspension and/or syrup, where the compound is mixed with a non-toxic suspending agent. Liquid oral dosage forms may also comprise one or more sweetening agent, flavoring agent, preservative and/or mixture thereof.

For rectal administration, a suitable composition containing vanoxerine, or a pharmaceutically acceptable salt, derivative or metabolite thereof, may be prepared in the form of a suppository. In addition to the active ingredient, the suppository may contain a suppository mass commonly used in pharmaceutical practice, such as Theobroma oil, glycerinated gelatin or a high molecular weight polyethylene glycol.

For parenteral administration, a suitable composition of vanoxerine, or a pharmaceutically acceptable salt, derivative or metabolite thereof, may be prepared in the form of an injectable solution or suspension. For the preparation of injectable solutions or suspensions, the active ingredients can be dissolved in aqueous or non-aqueous isotonic sterile injection solutions or suspensions, such as glycol ethers, or optionally in the presence of solubilizing agents such as polyoxyethylene sorbitan monolaurate, monooleate or monostearate. These solutions or suspension may be prepared from sterile powders or granules having one or more carriers or diluents mentioned for use in the formulations for oral administration. Parenteral administration may be through intravenous, intradermal, intramuscular or subcutaneous injections.

A composition containing vanoxerine, or a pharmaceutically acceptable salt, derivative or metabolite thereof, may also be administered nasally, for example by sprays, aerosols, nebulised solutions and/or powders. Metered dose systems known to those in the art may also be used.

Pharmaceutical compositions of vanoxerine, or a pharmaceutically acceptable salt, derivative or metabolite thereof, may be administered to the buccal cavity (for example, sublingually) in known pharmaceutical forms for such administration, such as slow dissolving tablets, chewing gums, troches, lozenges, pastilles, gels, pastes, mouthwashes, rinses and/or powders.

Compositions containing vanoxerine, or a pharmaceutically acceptable salt, derivative or metabolite thereof, for topical administration may comprise a matrix in which the pharmacologically active compound is dispersed such that it is held in contact with the skin in order to administer the compound transdermally. A suitable transdermal composition may be prepared by mixing vanoxerine, or a pharmaceutically acceptable salt, derivative or metabolite thereof, with a topical vehicle, such as a mineral oil, petrolatum and/or a wax, for example paraffin wax or beeswax, together with a potential transdermal accelerant such as dimethyl sulphoxide or propylene glycol. Alternatively, vanoxerine, or a pharmaceutically acceptable salt, derivative or metabolite thereof, may be dispersed in a pharmaceutically acceptable cream or ointment base. The amount of vanoxerine, or a pharmaceutically acceptable salt, derivative or metabolite thereof, contained in a topical formulation should be such that a therapeutically effective amount delivered during the period of time for which the topical formulation is intended to be on the skin.

Vanoxerine, or a pharmaceutically acceptable salt, derivative or metabolite thereof, may also be administered by continuous infusion either from an external source, for example by intravenous infusion or from a source of the compound placed within the body. Internal sources include implanted reservoirs containing the vanoxerine, or a pharmaceutically acceptable salt, derivative or metabolite thereof, to be infused which is continuously released for example by osmosis and implants which may be (a) liquid such as a suspension or solution in a pharmaceutically acceptable oil of the compound to be infused for example in the form of a very sparingly water-soluble derivative such as a dodecanoate salt or (b) solid in the form of an implanted support, for example of a synthetic resin or waxy material for the compound to be infused. The support may be a single body containing all the compound or a series of several bodies each containing part of the compound to be delivered. The amount of vanoxerine, or a pharmaceutically acceptable salt, derivative or metabolite thereof, present in an internal source should be such that a therapeutically effective amount is delivered over a long period of time.

In addition, an injectable solution of vanoxerine, or a pharmaceutically acceptable salt, derivative or metabolite thereof, can contain various additives such as preservatives, such as benzyl alcohol, methyl or propyl 4-hydroxybenzoate, benzalkonium chloride, phenylmercury borate and the like; as well as antioxidants, such as ascorbic acid, tocopherol sodium pyrosulfate and optionally complex forming agents, such as an ethylenediamine tetraacetate salt for binding the metal traces, as well as buffers for adjusting the pH value and optionally a local anaesthetizing agent, e.g. lidocaine. The injectable solution containing vanoxerine, or a pharmaceutically acceptable salt, derivative or metabolite thereof, is filtered before filling into the ampule and sterilized after filling.

Another preferred embodiment of the present invention is directed to a method of modulating the activity of an ion channel of a mammalian cell, such as a potassium ion channel, comprising contacting the mammalian cell with an effective amount of vanoxerine, or a pharmaceutically acceptable salt, derivative or metabolite thereof. According to such an embodiment of the present invention, the mammalian cell may be in vivo or ex vivo and the contacting step may be performed using any of the techniques known to those skilled in the art.

Another preferred embodiment of the present invention is directed to a method of screening for compounds that bind to $I_{Kr}$ or hERG comprising: (i) contacting a mammalian cell that stably expresses. $I_{Kr}$ or hERG with labeled vanoxerine, or a pharmaceutically acceptable salt, derivative or metabolite thereof, to form a labeled binding pair, (ii) contacting the labeled binding pair with a compound of interest; and (iii) determining whether the compound of interest displaces the labeled vanoxerine, or the pharmaceutically acceptable salt, derivative or metabolite thereof.

According to such embodiments, the vanoxerine, or the pharmaceutically acceptable salt, derivative or metabolite thereof, may be labeled with any suitable label, i.e. any label that does not interfere with the binding of the vanoxerine, or pharmaceutically acceptable salt, derivative or metabolite thereof, to $I_{Kr}$ or hERG. Illustrative examples of suitable labels include, but are not limited to, radio labels, such as certain hydrogen, sulfur and phosphorous atoms, and fluorescent labels. Such labels are known to those skilled in the art.

EXAMPLE

In a study conducted to measure the in vitro effect of vanoxerine, currents in mammalian cells stable transfected with the cloned human ether-a-go-go (hERG), hKvLQT1/hminK, rKv4.3, hKv1.5, and hHNa ion channel cDNAs, and native cardiac L-type calcium channel expressed in guinea pig cardiomyocytes (gpCaCh) were observed.

Voltage clamp currents from each cell were recorded continuously before and after equilibration with vanoxerine. Each cell acted as its own control and the effect of vanoxerine was quantified as the ratio, in each cell, of current magnitude after equilibration with vanoxerine to current magnitude in control. Nonlinear least squares fits of the current ratio data yielded the best fit value for the IC50 concentration. A positive control was included for each channel tested in the study.

| Vanoxerine Concentration-Response | |
|---|---|
| Channel | IC50 (μM) |
| hERG | 0.015 |
| hHNa | 0.57 |
| gpCaCh | 0.53 |
| HKvLQT1-hminK | 4.2 |
| rKv4.3 | 12.0 |
| hKv1.5 | 2.0 |

Under the experimental conditions (frequency of 0.1 Hz, corresponding to 6 beats per minute (bpm), at room temperature), vanoxerine blocked $I_{Kr}$ (hERG) channels in a concentration dependent fashion yielding an IC50 value of 150 nM. Vanoxerine block of hHNa (0.1 Hz, 6 bpm) was concentration dependent but the concentration-response relation was steeper than predicted by simple binding. A better fit to the data was obtained with the Hill equation with an IC50 estimate of 570 mM and a Hill coefficient of greater than 2.0.

Vanoxerine also blocked $I_{Kr}$ (hKv1.5) channels (0.1 Hz, 6 bpm) in a concentration dependent fashion yielding an IC50 value of 2.0 μM. Vanoxerine at a slower frequency (0.067 Hz, 4 bpm) blocked $I_{Ks}$ (hKvLQT1/hminK) channels in a concentration dependent fashion yielding an IC50 value of 4.2 μM. Vanoxerine blocked $I_{to}$ (rKv4.3) channels (0.067 Hz, 4 bpm) in a concentration dependent fashion yielding an IC50 value of 12.0 μM. At a slower frequency of 0.05 Hz, corresponding to 3 beats per minute, vanoxerine blocked cardiac calcium channel current ($I_{Ca,L}$) in a concentration dependent fashion yielding an IC50 value of 530 nM.

At doses of 1.0 M, vanoxerine had no effect on the duration of the cardiac potential in dog Purkinje fibers.

Because vanoxerine attains serum concentrations of about 100 nM at 100 mg doses for 1 week, the drug should block $I_{Kr}$, $I_{Ca}$ and $I_{Na}$. Therefore, refractoriness will be increased without the usual increase of $I_{Ca}$ or $I_{Na}$ that causes the early after-depolarizations that, in turn, trigger torsade de pointe and, consequently, VF. In addition, vanoxerine did not prolong the duration of the cardiac action potential, indicating that it should not prolong the QT interval of the electrocardiogram. It therefore appears that vanoxerine may be the most potent and safest drug for suppression of lethal cardiac arrhythmias.

More specifically, because of its pharmcodynamic actions on hERG and calcium channels and its pharmacokinetics (which assure appropriate levels for block of these channels), vanoxerine should be the most efficacious and safest antiarrhythmic drug for the treatment of atrial fibrillation and lethal ventricular arrhythmias.

The foregoing embodiments and advantages are merely exemplary and are not to be construed as limiting the present invention. The description of the present invention is intended to be illustrative, and not to limit the scope of the claims. Many alternatives, modifications, and variations will be apparent to those skilled in the art.

What is claimed is:

1. A method for maintaining normal sinus rhythm in a mammal that has previously exhibited atrial flutter or atrial fibrillation comprising administering to said mammal an effective amount of a compound selected from the group consisting of vanoxerine,
   1-[(2-(bis-(4-fluorophenyl)methoxy)ethyl]-4-(3-phenylpropenyl)-piperazine, 1-[(2-diphenylmethoxy)-ethyl]-4-(3-phenylpropenyl)-piperazine, and pharmaceutically acceptable salts thereof.

2. The method of claim 1, wherein a pharmaceutically acceptable salt of vanoxerine is administered.

3. The method of claim 2, wherein said pharmaceutically acceptable salt is selected from the group consisting of salts derived from hydrochloric acid, hydrobromic acid, sulfuric acid, sulfamic acid, phosphoric acid, nitric acid, acetic acid, propionic acid, succinic acid, glycolic acid, stearic acid, lactic acid, malic acid, tartaric acid, citric acid, ascorbic acid, pamoic acid, maleic acid, hydroxymaleic acid, phenylacetic acid, benzoic acid, salicylic acid, sulfanilic acid, 2-acetoxybenzoic acid, fumaric acid, toluenesulfonic acid, methanesulfonic acid, ethane disulfonic acid, oxalic acid, isethionic acid, trifluoroacetic acid, glutamic acid and aspartic acid.

4. The method of claim 1, wherein the mammal is a human.

5. The method of claim 1, wherein said vanoxerine or said pharmaceutically acceptable salt thereof is administered in combination with a pharmaceutically acceptable carrier or vehicle.

* * * * *